(12) United States Patent
Phillips et al.

(10) Patent No.: US 10,405,805 B2
(45) Date of Patent: Sep. 10, 2019

(54) COMBINED BLOOD FLOW AND PRESSURE MONITORING SYSTEM AND METHOD

(71) Applicant: USCOM LIMITED, Sydney, NSW (AU)

(72) Inventors: Robert Allan Phillips, Coffs Harbour (AU); Brendan Smith, Bathurst (AU)

(73) Assignee: USCOM LIMITED, Sydney (AU)

( * ) Notice: Subject to any disclaimer, the term of this patent is extended or adjusted under 35 U.S.C. 154(b) by 614 days.

(21) Appl. No.: 14/760,582

(22) PCT Filed: Jan. 14, 2014

(86) PCT No.: PCT/AU2014/000019
§ 371 (c)(1),
(2) Date: Jul. 13, 2015

(87) PCT Pub. No.: WO2014/107769
PCT Pub. Date: Jul. 17, 2014

(65) Prior Publication Data
US 2015/0351703 A1    Dec. 10, 2015

(30) Foreign Application Priority Data

Jan. 14, 2013 (AU) .............................. 2013900109

(51) Int. Cl.
*A61B 5/00* (2006.01)
*A61B 5/026* (2006.01)
(Continued)

(52) U.S. Cl.
CPC ............ *A61B 5/7278* (2013.01); *A61B 5/021* (2013.01); *A61B 5/022* (2013.01); *A61B 5/026* (2013.01);
(Continued)

(58) Field of Classification Search
CPC ....... A61B 8/4236; A61B 8/0891; A61B 8/42; A61B 8/065; A61B 8/0883; A61B 8/4416;
(Continued)

(56) References Cited

U.S. PATENT DOCUMENTS

| | | | |
|---|---|---|---|
| 5,865,749 A | * | 2/1999 | Doten ...................... A61B 8/06 600/443 |
| 6,565,513 B1 | | 5/2003 | Phillips |

(Continued)

FOREIGN PATENT DOCUMENTS

| | | | | |
|---|---|---|---|---|
| CN | 201409909 Y | | 2/2010 | |
| CN | 101919688 A | * | 12/2010 | ............... A61B 5/02 |

(Continued)

OTHER PUBLICATIONS

Sabbah, H., et al, "Noninvasive Evaluation of Left Ventricular Performance Based on Peak Aortic Blood Acceleration Measured With a Continuous-Wave Doppler Velocity Meter", Circulation, Journal of the American Heart Association, vol. 74, No. 2, Aug. 1986, pp. 323-329.

*Primary Examiner* — Bo Joseph Peng
(74) *Attorney, Agent, or Firm* — Pearne & Gordon LLP

(57) ABSTRACT

A method of blood flow monitoring for a patient, the method comprising the steps of: a) receiving a first signal indicative of the real time cardiac output for the patient; b) processing the continuous wave Doppler signal to provide an estimate of blood flow velocity as a function of time; c) receiving a pressure measurement indicative of the blood flow resistance through the patient; and d) calculating an Inotropy measure indicative of the potential and kinetic energy of the cardiac output of the patient.

5 Claims, 6 Drawing Sheets

(51) Int. Cl.
*A61B 5/021* (2006.01)
*A61B 5/02* (2006.01)
*A61B 5/145* (2006.01)
*A61B 8/06* (2006.01)
*A61B 8/08* (2006.01)
*A61B 8/00* (2006.01)
*A61B 5/022* (2006.01)
*A61B 5/029* (2006.01)

(52) U.S. Cl.
CPC .......... *A61B 5/029* (2013.01); *A61B 5/02028* (2013.01); *A61B 5/14542* (2013.01); *A61B 5/743* (2013.01); *A61B 8/065* (2013.01); *A61B 8/0883* (2013.01); *A61B 8/4236* (2013.01); *A61B 8/4416* (2013.01); *A61B 8/488* (2013.01); *A61B 8/5223* (2013.01); *A61B 8/0891* (2013.01); *A61B 8/42* (2013.01)

(58) Field of Classification Search
CPC ....... A61B 8/488; A61B 8/5223; A61B 5/022; A61B 5/029; A61B 5/7278; A61B 5/026; A61B 5/021; A61B 5/02028; A61B 5/743; A61B 5/14542
See application file for complete search history.

(56) References Cited

U.S. PATENT DOCUMENTS

| | | |
|---|---|---|
| 2010/0137717 A1 | 6/2010 | Strand |
| 2011/0137173 A1 | 6/2011 | Lowe et al. |
| 2012/0123246 A1 | 5/2012 | King et al. |

FOREIGN PATENT DOCUMENTS

| | | | | |
|---|---|---|---|---|
| JP | 2007-044408 | * | 2/2007 | ............... A61B 8/06 |
| WO | 2004084735 A1 | | 10/2004 | |
| WO | 2006096915 A1 | | 9/2006 | |
| WO | 2010103277 | | 9/2010 | |
| WO | 2011139297 A1 | | 11/2011 | |

* cited by examiner

COMBINED BLOOD FLOW AND PRESSURE MONITORING SYSTEM AND METHOD

FIELD OF THE INVENTION

The present invention relates to ultrasound monitoring of cardiovascular function and in particular to a system and method for combining flow and pressure measuring the cardiovascular system of a patient in order to determine a measure of inotropy.

The invention has been developed primarily for use with a Doppler monitoring system and provides real-time measures of cardiovascular function of a patient derived from continuous wave Doppler ultrasound and/or blood pressure measurements and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Cardiac performance is a function of the fluid flowing into the heart. The determinants of flow include, the preload, the performance of the heart (contractility and relaxation), and the afterload or systemic vascular resistance (SVR). However it is hypothesised that these parameters, while useful, do not completely describe cardiac function.

Importantly, the blood pressure (BP) is a product of the cardiac output (CO) and the vascular function, measured as SVR. A more complete representation of cardiovascular function will include combined measures of both flow and pressure.

The concept of Cardiac Power Output (CPO) and Stroke Work (SW) have been advanced as possible improvements to the basic assessment methods that can be derived from stroke volume (SV) and CO values, and BP.

An improved understanding of cardiovascular function can be determined by combining flow volume and pressure measures.

However, arterial pressure varies throughout the vascular network and so the point of measurement of the blood pressure is important when determining the usefulness and application of the measurement.

Currently Doppler is an accurate measure of blood flow but other accurate measures of flow could be utilised. While BP can be measured at any point in the cardiovascular network. The measurement methods vary from manometric methods located within the heart or vessels, acoustic sensors, plethysmography and tonometry. The science of each of these measurement methods is well established but their combination to create more informative measures of cardiovascular function which can be monitored has not been established.

Cardiac Power Output (CPO) in Watts is defined as effectively a product of mean Blood Pressure (BP) and Cardiac Output (CO).

Stroke Work (SW) is defined as the amount of energy in Joules that is given to the blood in a single heart stroke. With Cardiac Work (CW) further defined as the product of SW and the patient's heart rate.

CO and SV, which form the basis for calculating measures of CPO and SW, are typically measured using instantaneous single measures from echocardiography or invasive catheter derived measures. Previously, the most common method for calculating CPO and SW was Thermodilution, involving an invasive procedure based on the use of a pulmonary artery catheter (PAC) also known as the Swan-Ganz thermodilution catheter and provides a measure of right heart blood pressures. Using the PAC thermodilution CO can be measured, from which the CPO and SW can be derived.

These measures are typically made at one time and may take up to an hour to measure using invasive catheter methods. During this period the values of the measured parameters may change along with the patients condition. As CPO and SW vary beat to beat, reflecting changes in physiology and pathophysiology, a method of measuring SV and CO in real time for calculating CPO and SW will substantially improves these previously described methods.

Further the inclusion of more accurate and reliable measures of SV and CO may allow improved calculation of SW and CPO and may better describe cardiac and cardiovascular function.

Hence there is a need in the art for providing real-time, preferably non-invasive, measurement of the right and left ventricular blood flow of a patient and to provide a cardiac inotropy measure.

SUMMARY OF THE INVENTION

It is an object of the invention to provide an improved cardiovascular measurement and monitoring system and method.

In accordance with a first aspect of the present invention, there is provided a method of blood flow monitoring for a patient, the method comprising the steps of: a) receiving a first signal indicative of the real time cardiac output for the patient; b) processing the continuous wave Doppler signal to provide an estimate of blood flow velocity as a function of time; c) receiving a pressure measurement indicative of the blood flow resistance through the patient; and d) calculating an Inotropy measure indicative of the potential and kinetic energy of the cardiac output of the patient.

Preferably, the Inotropy measure can include an Inotropy Index combining a potential energy measure and a kinetic energy measure of the cardiac output. The Inotropy measure preferably can include a potential energy to kinetic energy ratio. The Inotropy measure preferably can include an Inotropy power measurement indicative of the time over which the cardiac output of the patient can be provided.

In some embodiments the predetermined blood flow measurement preferably can include one or more measurement selected from the set comprising: Ejection Time; Heart Rate; Peak Velocity, Velocity Time Integral and Mean Pressure Gradient.

In some embodiments, the first signal can comprise a continuous wave Doppler signal indicative of the cardiac output of the patient. The embodiments can include processing the continuous wave Doppler signal to provide an estimate of blood flow velocity comprising estimating a time sampled maximum velocity sequence.

Some embodiments can include processing the continuous wave Doppler signal to provide an estimate of blood flow velocity can comprise modelling flow velocity associated with at least one heart beat cycle as a series of line segment relating velocity to time.

In accordance with a further aspect of the present invention, there is provided a system to monitor blood flowing in a patient, the system comprising: first sampling unit for sampling a signal indicative of the cardiac output from the patient; second sampling unit for sampling a signal indicative of the arterial pressure of the patient; a processor interconnected to the first and second sampling unit and adapted to calculate an Inotropy measure indicative of the potential and kinetic energy of the cardiac output of the patient from the signal indicative of the cardiac output and signal indicative of the arterial pressure.

The Inotropy measure preferably can include a potential energy to kinetic energy ratio. The embodiments can also include processing the signal indicative of the cardiac output preferably can include a time sampled maximum velocity sequence of cardiac output.

In some embodiments, the processor further processes the continuous wave Doppler signal to provide an estimate of blood flow velocity which can comprise modelling flow velocity associated with at least one heart beat cycle as a series of line segment relating velocity to time.

In some embodiments the processor also calculates on or more measurement selected from the set comprising: Ejection Time; Heart Rate; Peak Velocity, Velocity Time Integral and Mean Pressure Gradient.

In accordance with a further aspect of the present invention, there is provided a computer-readable carrier medium carrying a set of instructions that when executed by one or more processors cause the one or more processors to carry out a method of blood flow monitoring for a patient, the method comprising the steps of: (a) receiving a continuous wave Doppler signal indicative of blood flowing in the patient; (b) receiving a pressure signal indicative of the blood pressure flowing in the patient; and (c) processing the continuous wave Doppler signal and pressure signal to provide a potential and kinetic energy measure as a function of time.

In accordance with a further aspect of the present invention, there is provided a method of calculating the blood flow myocardial power or inotropy of a patient, the method including the steps of: a) receiving a continuous wave Doppler signal indicative of blood flowing in the patient; a) processing the continuous wave Doppler signal to provide an estimate of blood flow velocity as a function of time; and b) receiving a second signal indicative of the pressure of blood flowing through the body of the patient; c) combining the two signals to produce an inotropy measure of the potential and kinetic energy developed by the heart.

The potential energy can be measured substantially from the difference between the mean arterial blood pressure and the central venous pressure. The kinetic energy can be measured substantially from the blood flow velocity. The kinetic energy can be measured substantially from the square of the time based integral of the blood flow velocity. The combining step further can comprise calculating a ratio of the potential energy to the kinetic energy.

BRIEF DESCRIPTION OF THE DRAWINGS

A preferred embodiment of the invention will now be described, by way of example only, with reference to the accompanying drawings in which.

PREFERRED EMBODIMENT OF THE INVENTION

Figure 1:
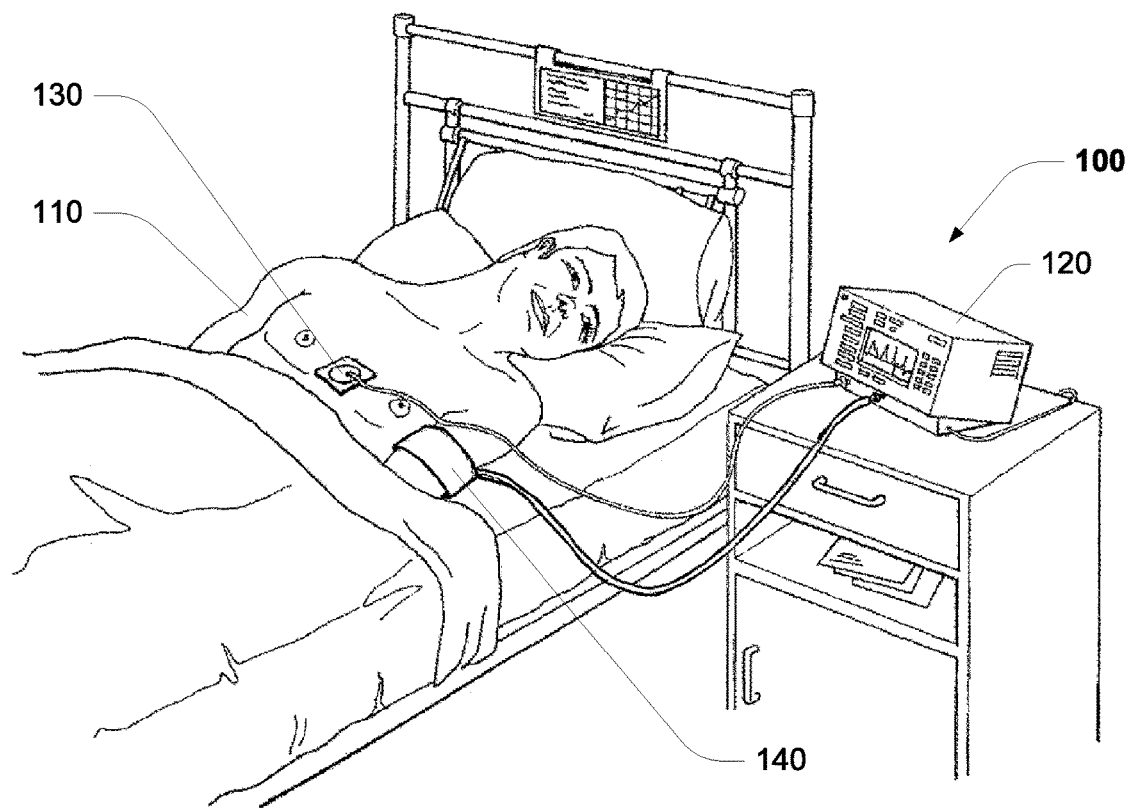
FIG. 1 is a perspective view of an arrangement of the preferred embodiment when utilised to monitor a patient according to the invention.

Monitoring of cardiovascular performance is important in many clinical environments. The circulation functions to transport oxygen and substrates to the tissues and returning the cell wastes for excretion. Blood is the transport medium of the circulation and caries the oxygen and substrates around a closed system within the body.

The blood is moved around this system primarily by the force of the heart, although the arteries and veins, muscular walled cylinders, also actively change diameter and thus resistance to the flow of blood thereby changing the load on the heart and the perfusion pressure of the BP. The heart functions as the pump in this system and the cardiac muscles rhythmically contract and relax changing the pressures within the chambers of the heart and driving the blood across the pressure gradients created by these contractions. The heart pumps into the vascular system against a resistance known as the afterload or systemic vascular resistance or the vascular compliance, which regulates the load on the heart and varies in response to the autonomic system to optimise the effectiveness of the circulation. This load on the heart can contribute to chronic or acute cardiac failure and optimisation of this resistance is a substantial objective of cardiovascular management.

Additionally, the heart is filled by venous blood returning to the heart, and this is often referred to as the preload and also related, via the Frank Starling mechanism, for the force of contraction of the heart. The interplay of these three dynamic entities modulates the circulation and ensures that oxygenated blood is delivered to the cells and de-oxygenated blood is returned to the lungs for oxygenation. The interplay of the preload, the cardiac function, and the afterload is fundamental to the efficiency of the circulation and is regulated on a beat to beat basis to optimise flow and pressure.

As the heart contracts the pressure in the left ventricle rises, the aortic valve opens and the pressure wave generated by the contraction of the ventricle is transmitted into the arterial tree. This pressure wave losses its energy the further it is from the generated source. However, at any point in the vascular system, the greater the contraction of the heart, the greater will be the pressure peak and it is possible to monitor the blood pressure, or equivalently pulse pressure, at any point in the circulation using a number of invasive or non-invasive methods. This changing pressure is the blood pressure and can be monitored to assess cardiac function.

These fluxing pressures can be monitored at a relatively subjective level using manual measure of the pulse, or as a quantitative measure using cuff or sphygmomanometric measurement of blood pressure. When the heart function is poor, the arterial pulse signals are diminished, while during increased output they are elevated. While the use of arterial pulse pressures to monitor cardiac function is established, it is clear that the pulse is a function of both the cardiac contraction and the vascular function including compliance, so that a strong pulse may be felt when cardiac function is poor but the vessels are constricted.

Blood pressure is commonly used as a measure of cardiac output, however the blood pressure is a function of the cardiac output and the vascular tone, BP=CO×SVR. This means that BP alone cannot be used as a measure of cardiac output, however in combination with measures of BP. In vivo, circulation is co-ordinated to preserve perfusion pressure, so a fall in cardiac output is often compensated for by a contraction of the arteries, resulting in an increase in SVR and therefore a preserved blood pressure. This results in blood pressure remaining relatively normal while CO is diminished and SVR increased. This may lead to inappropriate or incomplete management.

Additionally the relationship between pressures with the cardiovascular system can be used to generate multiple parameters related to speed and damping of the pressure wave within the cardiovascular system. The measurement at multiple sites within the circulation may allow the integration of multiple measures to create new and improved indices of cardiovascular performance.

Clearly indices that include both flow and pressure measures are a superior indicator of total cardiovascular well being and are superior predictors of mortality and morbidity. The weakness in these methods has been the unreliability and difficulty of acquiring the measures, and combining contemporaneous measures. The present application proposes a method which reliably, concurrently and simply provides such measures flow and pressure within the cardiovascular system which can be used to generate real-time flow pressure measures including CPO, SW and Inotrope measures, as well as new indices described below.

Referring to FIG. 1, there is provided an example embodiment of a system 100 for providing a measure of cardiac power of a patient 110. The system comprises a processing unit 120 adapted to receive and process a flow signal and the pressure signal for providing a measure of the cardiac power of the patient.

A transducer device 130 is used for monitoring flows within the patient and providing the flow signal. A blood pressure sensor 140 can be used for providing the pressure signal.

In this example embodiment, the transducer device is in the form of a continuous wave (CW) Doppler ultrasound transducer 130, having a typical operating frequency range of 1.0 to 3.0 MHz. This transducer element can be strapped to the left ventricular apical intercostal window, the left parasternal intercostal window or the suprasternal notch for monitoring transvalvular blood flows in the heart. The transducer is typically fixed in place with an adhesive sheet or tape, and a belt. The transducer monitors flows within the patient and is coupled to the computer signal processing unit 120 for providing the flow signal.

In an example embodiment, the blood pressure sensor 140 is in the form of a non-invasive sphygmomanometric source comprising a pressure gauge and a rubber cuff that wraps around the upper arm of the patient. In another embodiments, the blood pressure sensor comprises of an intra-arterial catheter. It is preferred that the blood pressure sensor 140 monitors the patient's blood pressure continuously and produces a pressure signal corresponding to the patient's systolic and diastolic blood pressure. The blood pressure sensor can be coupled to the computer signal processing unit 120 for providing the pressure signal.

There are a number of alternative methods by which these blood pressure signals can be converted to a quantitative measure of cardiovascular function. Two substantive methods for measuring a blood pressure signal include:

a) Invasive: arterial blood pressure monitoring using a manometer tipped catheter and positioning the transducer in the mid vessel so that flow dynamics are stable and representative. The smaller the artery the more noise from the measurement and the less accurate the signal, so the abdominal aorta is preferred however the internal iliac and radial artery can be accessed, and application in children is generally inaccurate and, due to invasiveness, undesirable.

b) Non-invasive: where a tonometer, acoustic sensor, sphygmomanometer, plethysmogram or Doppler is applied to the vessels at some point to sense the changes in BP. This is commonly at the medial cubital or radial arteries, however carotid, femoral, or peripheral pulses can also be measured. New oscillometric methods can now measure central BP and so would also be useful.

Each of these methods provides a simple blood pressure, or equivalently pulse pressure, signal indicating the sum of the cardiac and vascular performance. These signals are dependent on the diameter of the vessel and distance from the generator (heart), and the compliance of the vascular system.

However, in clinical practice it is preferred to understand both the cardiac and the vascular function individually as therapies are usually discrete and specific. For example, inotropes are used to stimulate cardiac contraction, while vasodilators relax the arterial vessel walls, dilating the artery, and reducing the vascular resistance, which in turn increases cardiac flow.

A simple measure of the blood pressure could be converted via a transfer function of constant (k) to calculate a quantitative cardiac output measurement, meaning that the blood pressure could be monitored as cardiac output. However, a limitation in this method is that blood pressure is a regulated variable, and as cardiac output drops as in disease, the arteries contract to maintain blood pressure and perfusion and as a result the method may monitor well in normal subjects, but is inaccurate in altered normal physiology or disease. Therefore the relationship between blood pressure and cardiac output varies.

Only over short periods of time, where the blood pressure signal was calibrated to a cardiac output measurement method, can monitoring blood pressure reflect changes in cardiac output. With an arterial manometer inserted and a blood pressure signal acquired, the blood pressure signal can be calibrated to an invasive transpulmonary thermodilution measurement of cardiac output. This calibration is recommended to be performed 8 hourly in stable monitoring, or whenever therapy is changed, the patient's position is changed, a therapy is introduced etc. Preferably the blood pressure signal should be calibrated beat to beat.

In an embodiment, as shown in FIG. 1, the transducer device 130 is a CW Doppler ultrasonic transducer that has been adapted for use as a heart monitoring device. CW Doppler is a well evaluated and a routine echocardiographic method of quantifying cardiac output with low inter and intra observational variability.

In the embodiment of a system 100 shown in FIG. 1, the CW Doppler can monitor both right and left ventriculo-arterial flow and can therefore measure CPO and SW of both the right and left ventricle. A pulmonary artery catheter, as it is lodged in the pulmonary artery, can only measures the flow across the pulmonary artery and so can only determine right ventricular CPO and SW.

U.S. Pat. No. 6,565,513 entitled "Ultrasonic Cardiac Output Monitor", the contents of which are incorporated herewith, measures this cardiac output accurately and non-invasively but requires a manual signal acquisition process to be carried out. Herein after referred to as the USCOM device. The USCOM device being available from USCOM limited of Sydney, Australia.

Direct measurement of transpulmonary flow can be achieved by applying a small CW Doppler transducer with an adherent gel coupling layer to the surface of the skin at the left parasternal acoustic window; adjacent to the sternum in an intercostal interspace, while the transaortic flow can be detected from the intercostal space associated with the palpable ventricular apex beat or from the suprasternal notch. The transducer can be fixed in place with adhesive tape or sheet and or a transthoracic belt utilising a thin gel coupling layer to ensure transducer skin contact.

Figure 2:
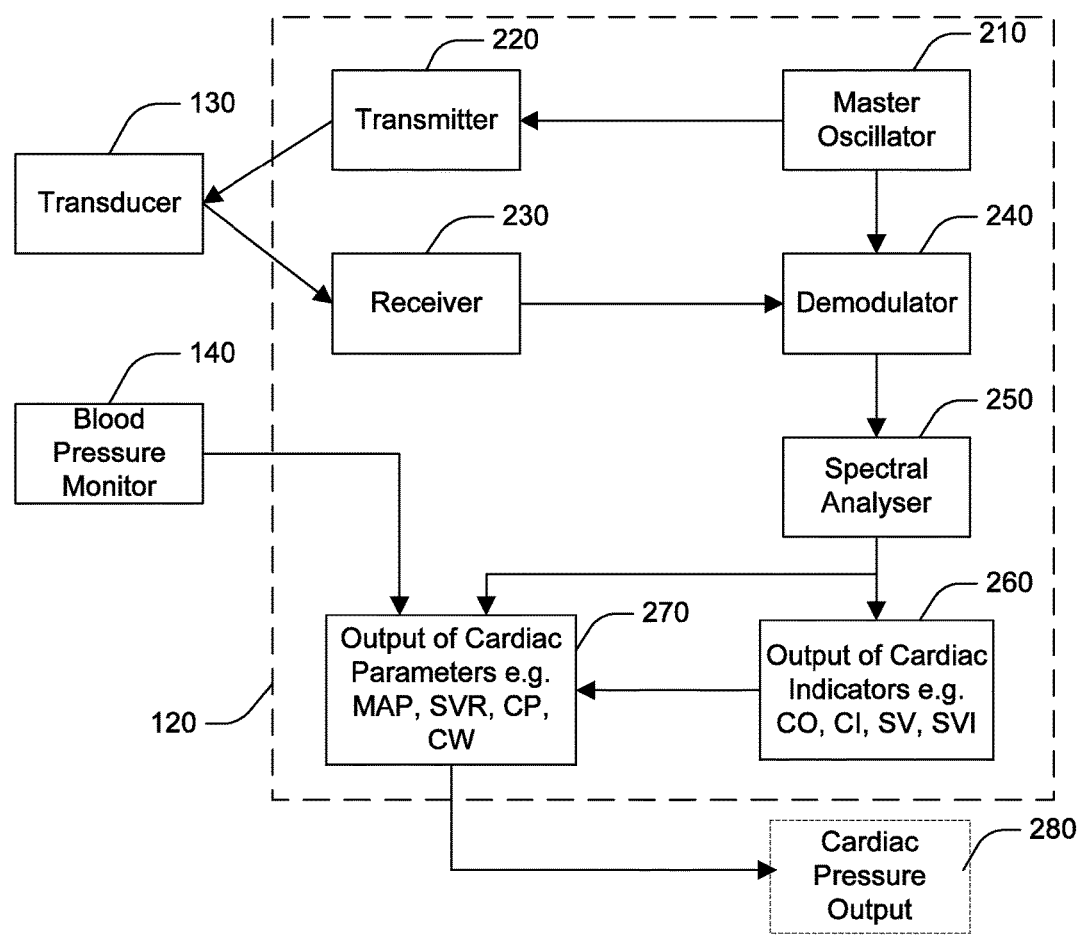
FIG. 2 is a functional block diagram of an embodiment of the invention.

Turning now to FIG. 2, there is illustrated in the form of a functional block diagram, an embodiment of the processing unit 120 shown in FIG. 1. This example processing unit includes a master oscillator 210 that is interconnected to a transmitter 220. The transmitter is configured to transmit the oscillation to transducer 230. A receiver 230 receives returned signals from the transducer 230, for further processing to produce a measure of cardiac output. The transducer signals are forwarded to a demodulating element 240, which utilises phase outputs from the master oscillator 210 to demodulate the transducer signals and provide for a spectral output. This spectral output is forwarded to a spectral analyser 250. In a preferred embodiment, the spectral analyser 250 includes a digital signal processor (DSP) arrangement for processing the spectral output to determine a number of relevant cardiac function indicators. In other embodiments, the spectral analyser 250 can comprise a computer type device with appropriate DSP hardware. Using common statistical data processing and analysis methods on the spectral output from the demodulator, a first processing component 260 can be configured to output a number of cardiac indicators. For example these cardiac indicators include:

a) Heart rate;
b) Cardiac index (CI): the amount of blood the left ventricle ejects into the systemic circulation in one minute, measured in liters per minute;
c) Stroke volume (SV): the amount of blood that is put out by the left ventricle of the heart in one contraction;
d) Stroke volume index (SV/): the quantity of blood ejected in one cardiac cycle in milliliters per meter square per beat; and
e) Cardiac output (CO): the amount of blood that is pumped by the heart per unit time, measured in liters per minute. CO can be calculated by multiplying the stroke volume by the heart rate.

As the master oscillator 210 is preferably able to provide a continuous signal to the transmitter 220 and hence the transducer 230, a continuous flow signal is provided to the receiver 230 and demodulator 240. This enables the cardiac indicators to be continuously updated, and hence provide real-time monitoring of cardiac indicators on a beat-to-beat basis. The real-time monitoring of cardiac indicators is commonly used for detecting and determining severity of cardiovascular disease and guiding therapy.

The real time monitoring can be implemented in a number of ways. For example, PCT application PCT/AU2006/000338 entitled "Automatic Flow Tracking System and Method", the contents of which are incorporated by cross reference, discloses one method of signal processing a real time spectral signal to extract the above cardiac indicators. Alternatively, semi-manual methods can be utilised for the extraction of parameters. An example of these procedures for manual tracing of the signal envelope are set out in PCT application PCT/AU2004/000343 entitled "Method of Tracing Geometric Elements", the contents of which are also incorporated by cross reference.

A blood pressure signal is provided by the blood pressure sensor 240 to a second processing component 270. The blood pressure signal provided the systolic and diastolic blood pressure values, which allows the second processing component 270 to calculate additional cardiac indicators. For example these additional cardiac indicators include:

a) Mean arterial pressure (MAP): the average pressure within an artery over a complete cycle of one heartbeat;
b) Systemic vascular resistance (SVR): an index of arteriolar constriction throughout the body, calculated by dividing the blood pressure by the cardiac output;
c) Cardiac Stroke Work (SW): the amount of energy that is given to the blood in a single heart stroke;
d) Cardiac Power Output (CPO): the product of mean Blood Pressure (BP) and Cardiac Output (CO).

Figure 3A:
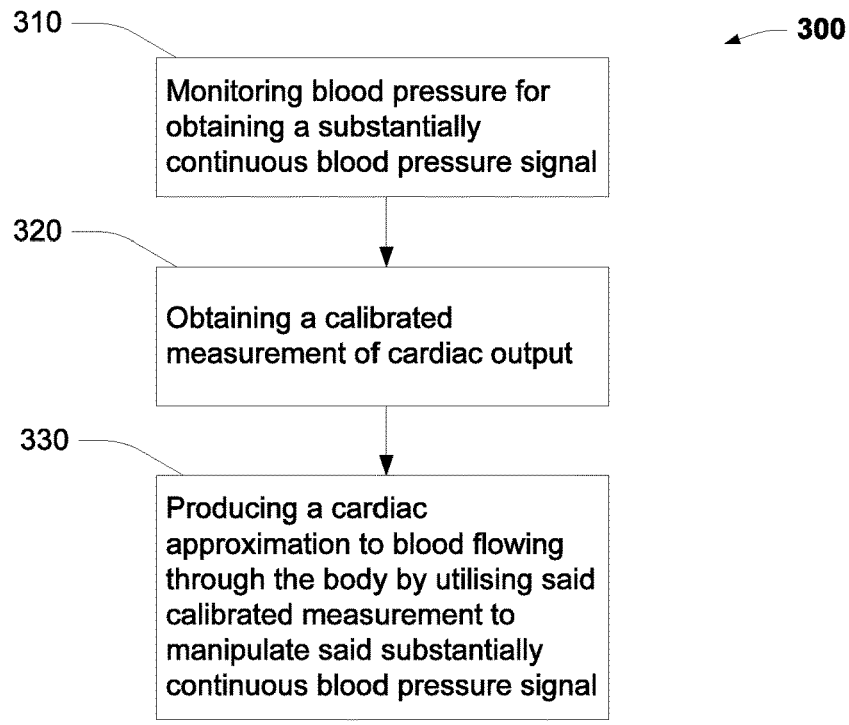
FIG. 3A shows a flowchart of method according to an embodiment.

FIG. 3A shows a flowchart of method 300. This method comprising the steps of:

a) Performing a substantially continuous blood pressure monitoring at a first predetermined location to obtain a substantially continuous blood pressure signal 310;
b) Obtaining a calibrated measurement of cardiac output 320 from a direct cardiac output device; and
c) Produce a cardiac approximation to blood flowing through the body by utilising the calibrated measurement to manipulate the substantially continuous blood pressure signal 330.

Figure 3B:
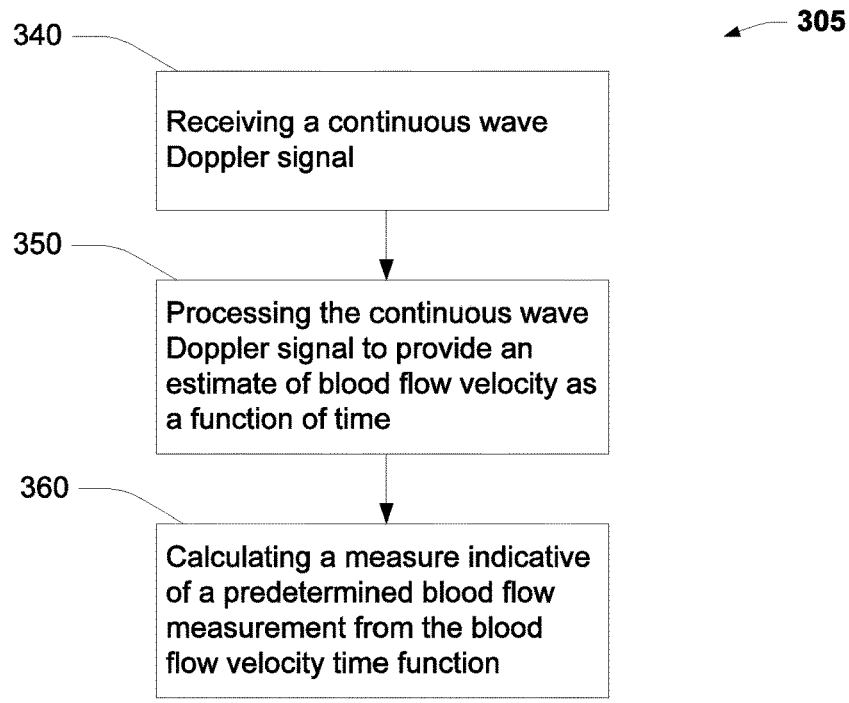
FIG. 3B shows a flowchart of alternative method according to an embodiment.

FIG. 3B shows a flowchart of alternative method 305. This method comprising the steps of:

a) receiving a continuous wave Doppler signal indicative of blood flowing in said patient 340;
b) processing said continuous wave Doppler signal to provide an estimate of blood flow velocity as a function of time 350; and
c) calculating a measure indicative of a predetermined blood flow measurement for said patient from said estimate of blood flow velocity 360.

Figure 4:
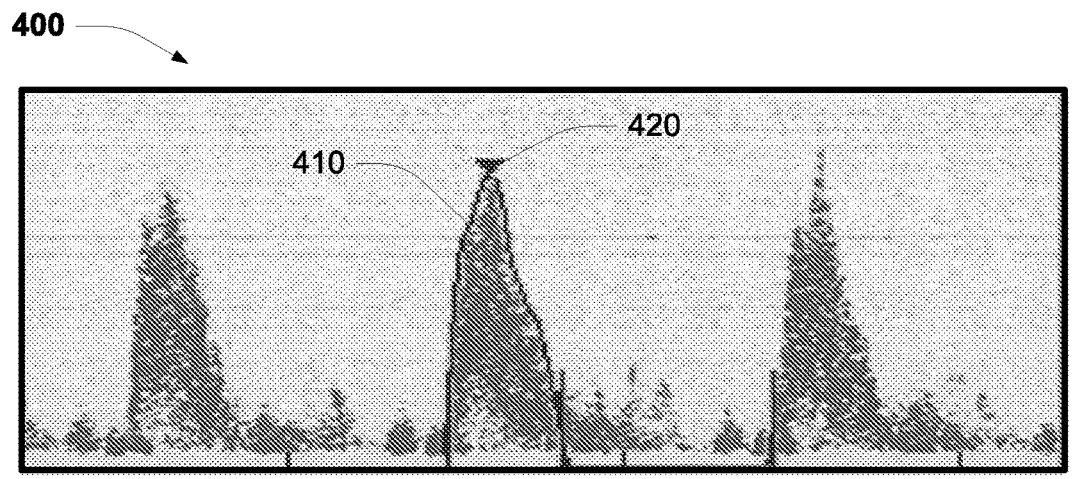
FIG. 4 illustrates continuous wave Doppler signals demonstrating pulsatile changes associated with changes in SV, and quantitative values of flow.

FIG. 4 illustrates a CW Doppler signal 400 demonstrating pulsatile changes associated with changes in SV, and quantitative values of flow. Each pulse, e.g. 410, corresponds to the blood flow during a single heart beat.

A Flow Tracer feature, outlined in the aforementioned applications, automatically traces the edge of the Doppler flow profile 410 to yield a substantially real time velocity curve. An estimation of Ejection Time, Heart Rate, Peak Velocity, Velocity Time Integral and Mean Pressure Gradient can be calculated from a Flow Tracer curve, as described below.

By way of example only, an embodiment utilises separate cardiac output monitoring to calibrate blood pressure signals to a standard base, thereby providing a calibrated continuous time signal of cardiac output.

Figure 5:
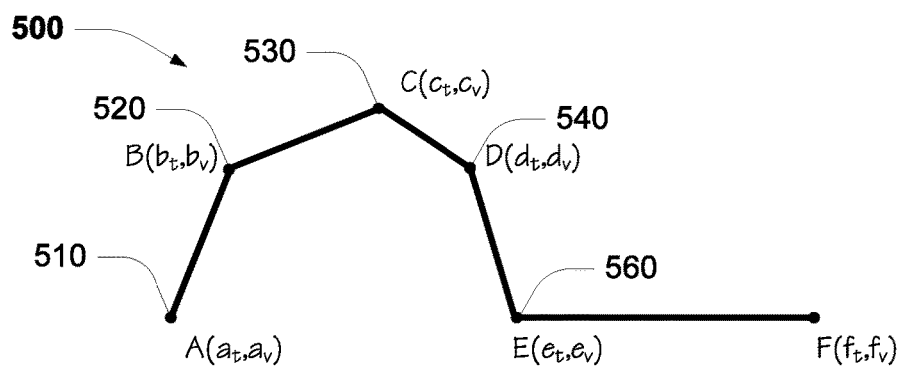
FIG. 5 shows an illustration of a "Touch Point" graph used in blood flow monitoring.

Turning now to FIG. 5, there is illustrated a "Touch Point" graph 500 used to model the Doppler flow profile. In this example, a Touch Point graph is defined by 6 points A-F, labelled 510, 520, 530, 540, 550 and 560 respectively. The horizontal axis is time (measured in seconds) and the vertical axis is velocity (measured in meters per second). It will be appreciated that the Touch Point graph is used to represent the shape of the Doppler flow profile of a single heartbeat.

In an embodiment, constraints can be placed on the time or velocity values of the selected points 510, 520, 530, 540, 550 and 560. For example the velocity value assigned to B 520 (i.e. $b_v$) and D 540 (i.e. $d_v$) may be constrained such they remain equal. For example the velocity value assigned to A 510 (i.e. $b_v$), E 550 (i.e. $e_v$) and F 560 (i.e. $f_v$) may be constrained such they remain constant and/or set to zero.

Referring back to FIG. 3B, it will be appreciated that processing the continuous wave Doppler signal to provide an estimate of blood flow velocity as a function of time 350 includes the Flow Tracer estimate and Touch Point estimates.

The Flow Traces estimate provides an estimate of blood flow velocity, and comprises estimating the maximum velocity at each time sample.

The Touch Point estimate provides an estimate of blood flow velocity, and comprises modelling the velocity associated with at least one heart beat cycle as a series of line segment relating velocity to time. Preferably, the series of line segments are defined by at least 6 calculated data points, thereby comprising at least 5 line segments. It will be appreciated that multiple heart beat cycles can be modelled with this method, typically requiring further line segments.

Cardiac Power (CPo) and stroke work (SW) are indices that can be used as a measure of cardiovascular performance. These indices have a correlation with predictivity in heart failure. They have further been derived to show a relationship between CO or SV and blood pressure, typically expressed as MAP (mean arterial pressure).

To calculate myocardial power or inotropy it is necessary to measure the potential and kinetic energy developed by the heart, which is the external cardiac work, and then divide this by the flow time, the time taken to do this much work. Potential Energy is the energy used to produce blood pressure. Kinetic Energy is the energy used to produce blood flow.

Potential Energy is the product of change of pressure and the change of volume or $PE = \Delta P \times \Delta V$. The change in pressure, $\Delta P$, is the mean blood pressure—CVP, or the pressure of the blood coming out of the heart minus the pressure that the blood came in to the heart. While Kinetic Energy for any moving mass is given by the formula $KE = \frac{1}{2} mV^2$, where m is the mass of the object and V its velocity.

Thus knowing pressure and flow, CO/SV and BP additional parameters can be calculated. A relationship between the CO and MAP is presented, which results in new parameters of cardiovascular performance being Inotropy Index (INO), Potential Energy to Kinetic Energy ratio (PE:KE) and Potential Kinetic Energy Product (PKEP).

Calculation of Inotropy Index (INO), Potential Energy to Kinetic Energy ratio (PE:KE), Potential Kinetic Energy Product (PKEP), Ejection Time, Heart rate, Peak Velocity, Velocity Time Integral and Mean Pressure Gradient are described below. These values can be directly calculated or estimated using the following techniques and/or equations.

Inotropy Index

Inotropy Index (INO) can be calculated in the following way.

Inotropy can be viewed as the average energy of the blood over the period of systole. This has two components: the potential energy component (P) and the kinetic energy component (K). Since it is an average energy over time, the units are Watts.

Inotropy Index $= P + K$

Where: P = Stroke Work/Flow Time. And, $$K = \frac{\frac{1}{2} m \overline{v^2}}{FT}$$

where the numerator is a kinetic energy term. This is then averaged over the period of systole. m is the mass of a single stroke of blood, v is the instantaneous velocity of the blood during systole. $\overline{v^2}$ denotes the average of all the velocity squared values over this period.

To calculate potential energy (P) we can use the mean blood pressure which is the difference between mean arterial pressure and central venous pressure (BPmn=MAP−CVP). For kinetic energy (K), using the blood flow monitor, we can use the integral of velocity squared which is the Mean Transvalvular Pressure Gradient (Pmn). Hence we can calculate the kinetic energy (K):

$$P_{mn} = \frac{4}{FT_s} \int_0^{FT_s} (v(t))^2 dt$$

$$\text{Inotropy Index}_W = \frac{BPm_{mmHg} \cdot SV_{ml} \cdot 10^{-3}}{7.5 \, FT_s} + \frac{BD_{kg/m^3} \cdot Vpk_{m/s}^2 \cdot SV_{ml} \cdot 10^{-6}}{2 FT_s}$$

$$= \frac{(MAP_{mmHg} - CVP_{mmHg}) \cdot SV_{ml}}{7.5 \, FT_{ms}} + \frac{\frac{1}{2} \overbrace{(BD_{kg/m^3} \cdot SV_{ml} \cdot 10^{-6})}^{mass} \cdot \overbrace{\left( \frac{1}{FT_s} \int_0^{FT_s} (v(t))^2 dt \right)}^{\overline{v^2}}}{FT_s}$$

$$= \frac{1}{FT_{ms}} \overbrace{\left( \frac{60}{450} (MAP_{mmHg} - CVP_{mmHg}) \cdot SV_{ml} \right)}^{Stroke\ Work} + \frac{\frac{1}{2}(BD_{kg/m^3} \cdot SV_{ml} \cdot 10^{-6}) \cdot \frac{Pmn_{mmHg}}{4}}{FT_{ms} \cdot 10^{-3}}$$

$$= \frac{SW_{mJ}}{FT_{ms}} + \frac{BD_{kg/m^3} \cdot Pmn_{mmHg} \cdot SV_{ml} \cdot 10^{-3}}{8 \, FT_{ms}}$$

Hence an Inotropy Index can be calculated using the formula:

$$\text{Inotropy Index}_W = \frac{SW_{mJ}}{FT_{ms}} + \frac{BD_{kg/m^3} \cdot Pmn_{mmHg} \cdot SV_{ml} \cdot 10^{-3}}{8 \, FT_{ms}}$$

where: SW is Stroke Work (mJ):

$$SW_{mJ} = \frac{60}{450} (MAP_{mmHg} - CVP_{mmHg}) \cdot SV_{ml},$$

MAP is Mean Arterial Pressure, CVP is central venous pressure, FT is flow time (ms), BD is blood density $$(kg/m^3) \approx 1010_{kg/m^3} + \frac{1}{3} Hb_{g/L} = 1058.3 \text{ kg/m}^3$$

with the default value of 145 g/L for Haemoglobin; being a national average value, Pmn is Mean Pressure Gradient (mmHg) and SV is Stroke volume (ml)

Inotropy, in joules, is effectively the SW divided by the ejection time. SW is an important measure of the work of the heart during a single beat. However the work of the heart is actually performed only during systole, approximately ⅓ of the total cardiac cycle, so any calculation of work to the full duration of the cardiac cycle, will result in an average work. Inotropy was conceived to address this by considering that the power of a single contraction is performed only while the aortic or pulmonary valve is open, or the ejection time. Dividing the SW by the ejection time, a parameter simply derived from the Doppler cardiac output flow profile, results in a more accurate measure of the contractile force of the heart and results in a parameter reflective of total cardiac power or inotropy. This is a new parameter only determined by combining Doppler ultrasound CO measures and central pressure measures.

Potential Energy to Kinetic Energy Ratio (PKR)

The ratio between the kinetic and potential energy components in the Inotropy index may be clinically useful and have a precedent in the pressure rate product previously used as a means of determining cardiovascular performance. This parameter provides insights into the relationship between flow and pressure and may be a useful clinical tool.

Potential Energy to Kinetic Energy ratio (PE:KE) can be expressed mathematically by the following equation:

$$PE:KE \text{ ratio} = \frac{\frac{SW_{mJ}}{FT_{ms}}}{\frac{BD_{kg/m^3} \cdot Pmn_{mmHg} \cdot SV_{ml} \cdot 10^{-3}}{8FT_{ms}}}$$

$$= \frac{8 \cdot 1000 \cdot SW_{mJ}}{BD_{kg/m^3} \cdot Pmn_{mmHg} \cdot SV_{ml}}$$

$$= \frac{8 \cdot 1000 \cdot \left(\frac{60}{450}(MAP_{mmHg} - CVP_{mmHg}) \cdot SV_{ml}\right)}{BD_{kg/m^3} \cdot Pmn_{mmHg} \cdot SV_{ml}}$$

$$= \frac{8 \cdot 1000 \cdot \frac{60}{450}}{BD_{kg/m^3}} \cdot \frac{(MAP_{mmHg} - CVP_{mmHg})}{Pmn_{mmHg}}$$

As $$BD_{kg/m^3} \approx 1010_{kg/m^3} + \frac{1}{3}Hb_{g/L}$$

and the clinical range of Hb is 75-180, with an average of 145. The blood density is hence very close to 1060.

Substituting this into the above formula gives a constant value of 1.0006, which is close enough to 1.0000. Hence a fair simplification of this formula is $$PE:KE \text{ ratio} = \frac{(MAP_{mmHg} - CVP_{mmHg})}{Pmn_{mmHg}}$$

Kinetic Potential Energy Product (KPEP)

Kinetic Potential Energy Product (KPEP) can be expressed mathematically by the following equation.

KPEP=P×K

KPEP=Pmn×(MAP−CVP). Assuming CVP≅0 we get KPEP=Pmn×MAP, where K=Pmn; P=BPmn=MAP−CVP, or simplified to MAP.

Cost of Delivery Index

The objective of the circulation is to deliver oxygen to the cells of the body. While SW describes the combined cardiovascular energy of a single beat, a method to relate this energy expenditure relative to the volume of oxygen delivered to the tissues is useful. With the input of blood oxygen saturation, usually by an SpaO2 monitor, and haemoglobin concentration, Doppler ultrasound can calculate DO2, or the volume of oxygen delivered from the heart. Theoretically, the energy to deliver this volume of oxygen should be an important insight into the efficiency of the cardiovascular system. It is proposed that the cost of delivery which is the work to deliver one liter of oxygen per minute to the body. To improve the inter subject comparison of this parameter, this value should be indexed to body weight, so that the cost of delivery index is the work required to deliver one liter of oxygen to one kilogram of tissue with units are mJ/L/min/Kg, or SW/DO2/wt(kg).

Peak Velocity

Peak Velocity ($V_{pk}$) is the maximum velocity during the stroke ejection time. A peak velocity trace "Flow Tracer" can be drawn, and used, to identify the peak velocity. Alternatively, automated image processing techniques can be used. Referring to FIG. 4, Peak Velocity ($V_{pk}$) is the maximum velocity traced 420 during the stroke ejection time.

Figure 6:
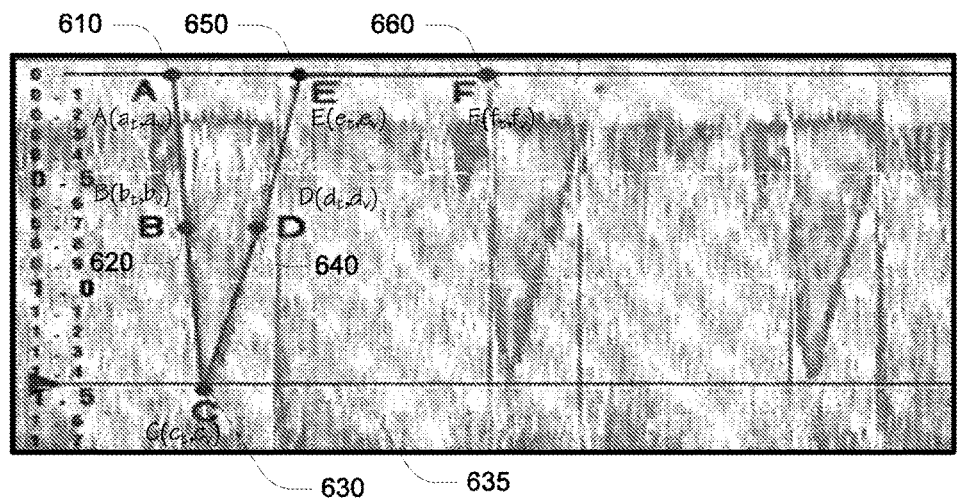
FIG. 6 illustrates continuous wave Doppler signals identifying features used in blood flow monitoring.

Referring to FIG. 6, an example CW Doppler signal is shown with an overlay series of Touch Points defined by 6 points A-F, labelled 610, 620, 630, 640, 650 and 660 respectively. In this example, the Peak Velocity (Vpk) can be identified by point labelled C 630. A peak velocity trace 635 can be drawn to identify the peak velocity.

Pressure Gradient

It will be appreciated that an instantaneous Pressure Gradient (ΔP) can be approximated by the use of a modified Bernoulli Equation, as expresses below:

$$\Delta P = P_2 - P_1 = 4V^2 \text{ (mmHg)}$$

A Mean Pressure Gradient ($P_{nm}$) can be further calculated as the mean of the instantaneous Pressure Gradient over the respective stroke ejection time. This can be expressed as the average of the function $4V^2$ over the flow period.

The mean pressure gradient ($P_{nm}$), for a single heartbeat, is derived by calculating the integral of $4V^2$ over the flow period. The average value of $4V^2$ can then expressed in units of mmHg, as shown in the following equation. This equation can be used to calculate $P_{nm}$ over the flow period identified by the Flow Trace 410.

$$P_{mn} = \frac{4}{\text{flow period}} \int_{\text{flow start}}^{\text{flow stop}} (v(t))^2 \, dt \text{ (mmHg)}$$

Referring to FIG. 6, in this example, the flow period interval for Touch Point extends from A 610 though E 650, as represented by [$a_t, e_t$]. The average of a function ($f_{av}$), over a time interval [$a_t, b_t$] can be expressed mathematically by the following equation.

$$f_{av} = \lim_{n \to \infty} \frac{1}{b_t - a_t} \sum_{i=1}^{n} f(x_i^*) \Delta x$$

$$= \frac{1}{b_t - a_t} \int_a^b f(x) \, dx$$

In a discrete time (sampled) environment, where n samples are taken (for example Δt=10 ms) over the stroke ejection interval [$a_t, e_t$], the Mean Pressure Gradient can be expressed mathematically by the following equation.

$$P_{mn} = \frac{1}{e_t - a_t} \sum_{i=1}^{n} (4V^2)\Delta t$$

Thus, by calculating $V^2$ for each sample over the stroke ejection interval $P_{mn}$ can be derived. However, it will be appreciated that V itself is derived from a series of straight-line approximations between each of the "grab-points" on the monitor trace output. This allows the average value of $V^2$ to be directly calculated for each segment, rather than using the discrete form and summing the $V^2$ values for each sample.

For each straight-line segment, the equation for V is expressed as a function of time, t. It will be appreciated that the equation for a straight line is represented in the following equation, where $m=(y_2-y_1)/(x_2-x_1)$ and $c=y_1-mx_1$; $y=mx+c$ Therefore, an equation for V as a function of time (t) can be expressed in the following form: $V=mt+c$ The Mean Pressure Gradient ($P_{mn}$), being the average of the function $4V^2$ over the first segment $[a_t,b_t]$, can be expressed in the following form.

$$P_{mn} = \frac{1}{b_t - a_t} \int_a^b 4V^2 \, dt$$

$$= \frac{1}{b_t - a_t} \int_a^b 4(mt+c)^2 \, dt$$

$$= \frac{4}{b_t - a_t} \left[ \frac{m^2}{3}t^3 + mct^2 + c^2 t \right]_a^b$$

It will further be appreciated that the average value over the entire stroke ejection interval $[a_t,e_t]$ can be calculated as follows:

$$p_{mn} = \frac{4 \sum_{i=1}^{4} \left[ \frac{m_i^2}{3}t^3 + m_i c_i t^2 + c_i^2 t \right]_{a_i}^{b_i}}{e_t - a_t} \text{ (mmHg)}$$

Velocity Time Integral

The Velocity Time Integral (vti) can be identified as the "area under the curve" of the Doppler flow profile during the stroke ejection time.

Referring to FIG. 4, an area defined by the Flow Tracer 410 can be used to estimate vti. The velocity of the Doppler flow profile is available for each 10 ms spoke of the signal.

Figure 7:
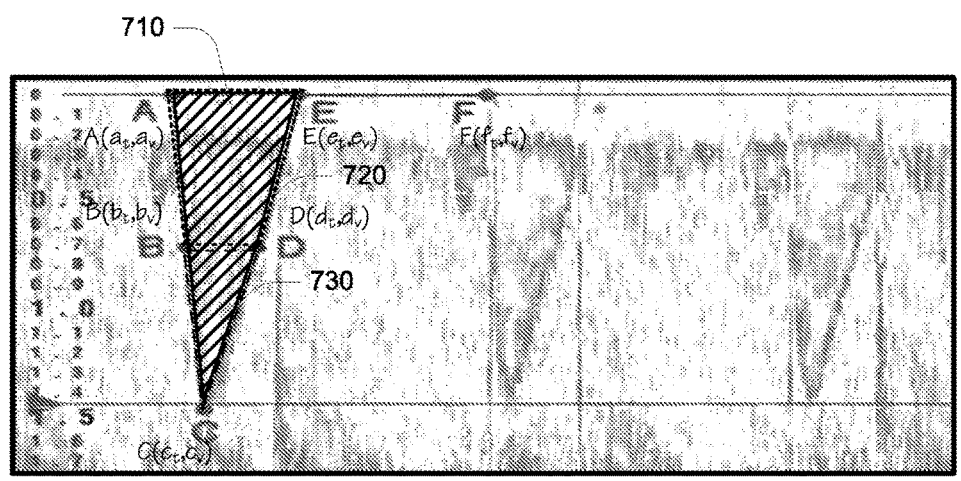
FIG. 7 illustrates continuous wave Doppler signals identifying features used in blood flow monitoring.

Referring to FIG. 7, an example Velocity Time Integral (vti) can be identified as the area of the displayed Touch Point Doppler flow profile, as indicated by the shaded area 710. It will be appreciated that the Velocity Time Integral (vti) is indicative of the stroke distance, or the distance a single red blood cell travels per beat cycle.

In this example, the Touch Point velocity curve is approximated by a series of straight-line segments. The area under this velocity curve can be further partitioned into a trapezoid 720 and a triangle 730.

In an embodiment, it will be appreciated that the value for vti derived from using the Touch Point curve can be modified by a correction factor ($KTP_{vti}$). The use of a correction factor is discussed below.

A Velocity Time Integral (vti) can be calculated using the area under the flow portion of the velocity trace. By way of example, velocity of the Doppler flow profile is available for each 10 ms spoke of the signal. The area value obtained can be further increased using a correction factor $KFT_{vti}$ to calculate a measure of vti, as shown in the following equation.

$$VTI = KFT_{vti} \left( \int_{flow\ start}^{flow\ end} v(t) \, dt \right) \times 100 \text{ (cm)}$$

Therefore, a Velocity Time Integral (vti) calculated from the area under the velocity curve can be calculated using the following equation.

$$VTI =$$
$$KTP_{vti}\left(\frac{1}{2}((e_t - a_t) + (d_t - b_t))(b_v - a_v) + \frac{1}{2}(d_t - b_t)(c_v - b_v)\right) \times 100 \text{ (cm)}$$

Ejection Time

Figure 8:
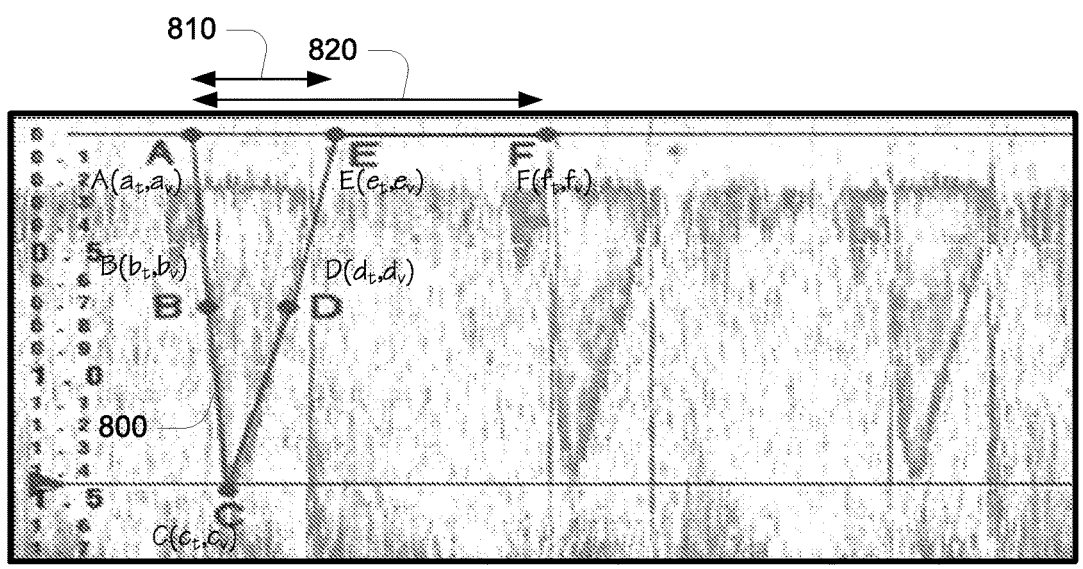
FIG. 8 illustrates continuous wave Doppler signals identifying features used in blood flow monitoring.

Ejection Time ($t_{ET}$) is defined the duration of systole in seconds. For Flow Tracer heartbeats, the ejection time can be calculated as duration of the flow. The Ejection Time ($t_{ET}$) can be identified as flow end time less the flow start time. Referring to FIG. 8, using the Touch Point curve 800 an Ejection Time ($t_{ET}$) can be identified as the time between points E and A, as represented by the line segment 810. This can be expressed mathematically by the following equation.

$$t_{ET} = e_t - a_t \text{ (sec)}$$

Flow Time (FT) is typically expressed as an ejection time ($t_{ET}$) in milliseconds, as expressed in the following equation.

$$FT = t_{ET} \text{ (ms)}$$

Heart Rate

Heart Rate (HR) is described as the beat frequency, which is typically measured in beats per minute. HR is the reciprocal of the beat time ($t_{HR}$) between the start of the current heartbeat and the start of the next heartbeat, as expressed in the following equation.

$$HR = \frac{1}{t_{HR}}$$

Referring to FIG. 8, using the Touch Point curve 800 a beat time ($t_{HR}$) can be identified as the time between points A and B, which is represented by the line segment 820 and expressed mathematically in the following equation.

$$t_{HR} = f_t - a_t \text{ (sec)}$$

Heart Rate can therefore be expressed in the following equation. It will be appreciated that the multiplying factor of 60 is to convert the measurements from beats per second to beats per minutes.

$$HR = \frac{60}{f_t - a_t} \text{ (beats/min)}$$

Minute Distance

Minute Distance (MD) is the distance a single red blood cell travels per minute, and can be expressed mathematically as shown in the following equation.

$$MD = HR \times VTI$$

Referring to FIG. 8, using the Touch Point curve 800 a Minute Distance (MD) can be calculated using the following equation. It will be appreciated that vti is typically reported in cm and MD is typically reported in m/min, which using the above equations requires a conversion factor of 1/100.

$$MD = HR \times VTI = \left(\frac{60}{f_t - a_t}\right) \times \left(KTP_{vti}\left(\frac{1}{2}((e_t - a_t) + (d_t - b_t))(b_v - a_v) + \frac{1}{2}(d_t - b_t)(c_v - b_v)\right)\right) \text{ (m/min)}$$

Ejection Time

Ejection Time (ET %) is the ratio of ejection time to beat time, and can be expressed mathematically as shown in the following equation.

$$ET\ \% = \frac{t_{ET}}{t_{HR}}$$

Referring to FIG. 8, using the Touch Point curve 800 an Ejection Time (ET %) can be calculated using the following equation.

$$ET\ \% = \frac{e_t - a_t}{f_t - a_t}$$

Stroke Volume

Stroke Volume (SV) is the volume of blood passing through the Aortic or Pulmonary Artery (depending on mode of operation or the system) during a single heart beat cycle. This measure is typically expressed in $cm^3$. To calculate Stroke Volume, an estimate of the Output Tract Diameter (OTD) is typically used. This is typically the aortic or pulmonary tract diameter (again depending on mode of operation) and depends on the Doppler signal source.

Output Tract Diameter (OTD) can be estimated from height—for patients over 50 cm tall. Alternatively, Output Tract Diameter (OTD) can be calculated from weight—for patients less than 50 cm tall. It will be appreciated that a weight based estimation algorithm is generally intended for use in the case of small babies. Height Based OTD (Patient Height≥50 cm) utilises a proportional relationship between height and OTD for both Aortic and Pulmonary output tracts. A regression equation for aortic tract diameter can be expressed mathematically as shown in the following equation.

$d_{AV}$=0.010×height+0.25 cm

A proportional relationship between aortic and pulmonary output tract diameters ($d_{av}$ and $d_{pv}$ respectively) has been further identified. This proportional relationship is primarily supported by experimental data. This relationship is described mathematically by the following equation.

$d_{PV}$=1.097×$d_{AV}$ $d_{PV}$≅0.011×h+0.274

Ninety-five percent (95%) confidence intervals for the predicted values using the above formulas for estimating $d_{av}$ and $d_{pv}$ are described by:

$d_{AV}$=0.010×height+0.25 cm±0.27 cm $d_{PV}$=(1.097±0.208)$d_{AV}$

A correction factor ($K_{OTD}$) can be used to increase the OTD derived from these formulas. The estimated OTDs used can therefore be described mathematically by the following equations. This correction factor ($K_{OTD}$) is described in more detail below.

$d_{AV}$=$K_{OTD}$(0.010×height+0.25) cm $d_{PV}$=$K_{OTD}$(0.011×h+0.274) cm

Weight Based OTD (Patient Height<50 cm) for estimating aortic and pulmonary output tract diameters ($d_{av}$ and $d_{pv}$ respectively) can be expressed mathematically by the following equations. It will be appreciated that in these equations the weight is measured in kilograms.

$d_{AV}$=0.093×weight+0.343 cm $d_{PV}$=0.100×weight+0.368 cm

From aortic and/or pulmonary output tract diameters ($d_{av}$ and $d_{pv}$ respectively) a stroke volume can be calculated. The Stroke Volume (SV) is the volume of blood passing through the Aortic or Pulmonary Artery (depending on mode of operation) in $cm^3$.

SV=CSA×vti

In the above equation, $$CSA = \frac{\pi d_{AV}^2}{4}$$

for Aortic OTD and $$CSA = \frac{\pi d_{AV}^2}{4}$$

for Pulmonary OTD.

For Aortic OTD based calculation of stroke volume an estimate can be expressed mathematically by the following equation.

$$SV = CSA_{AV} \times vti$$
$$= \pi r_{AV}^2 \times vti$$
$$= \pi \times \frac{(0.01 \times h + 0.25)^2}{4} \times vti\ (cm^3)$$

For Pulmonary OTD based calculation of stroke volume an estimate can be expressed mathematically by the following equation.

$$SV = CSA_{PV} \times vti$$
$$= \pi r_{PV}^2 \times vti$$
$$= \pi \times \frac{(0.011 \times h + 0.274)^2}{4} \times vti\ (cm^3)$$

Stroke Volume Index

Stroke Volume Index (SVI) can be estimated using the following equation.

$$SVI = \frac{SV}{BSA} \text{ (ml/m}^2\text{)}$$

Stroke Volume Variation

Stroke Volume Variation (SVV) is the variation of Stroke Volume over a group comprising a number of heart beat cycles.

An estimate of Stroke Volume Variation (SVV) can be calculated using the following equation.

$$SVV = \frac{SV_{max} - SV_{min}}{\frac{SV_{max} + SV_{min}}{2}} \text{ (\%)}$$

Cardiac Output

A Cardiac Output (CO) can be calculated using the following equation.

$$CO = \frac{SV \times HR}{1000} \text{ (liters/min)}$$

Cardiac Index

A Cardiac Index (CI) can be calculated using the following equation.

$$CI = \frac{CO}{BSA} \text{ (liters/min/m}^2\text{)}$$

It will be appreciated that, in order to calculate an estimate of Cardiac Index (CI) an estimate of Body Surface Area (BSA) is required. An estimate of BSA can be calculated from the height and weight values (typically entered by an operator) using Boyd nomogram as expressed mathematically in the following equation.

BSA=0.0003207×height$^{0.3}$×(weight× 1000)$^{(0.7285-0.0188\times(3.0+log\ 10(weight)))}$ (m$^2$)

In an embodiment, when patient data is exported, the BSA can be calculated using this formula. It will be appreciated that numerical problems may exist if the weight is set as zero, due to the $\log_{10}($ ) term. To avoid this problem, at least computationally, a modified formula can be used so that zero height or weight is handled without numerical errors. A 0.00001 kg term is added to the weight in the $\log_{10}($ ) term of the above equation to provide the following BSA estimate equation.

BSA=0.0003207×height$^{0.3}$×(weight× 1000)$^{(0.7285-0.0188\times(3.0+log\ 10(weight+0.00001)))}$(m$^2$)

Mean Arterial Pressure

A Mean Arterial Pressure (MAP) can be calculated using the following equation. In this equation, $BP_{sys}$ is Systolic Blood Pressure (mmHg) and $BP_{dia}$ is Diastolic Blood Pressure (mmHg). It will be appreciated that $BP_{sys}$ and $BP_{dia}$ may be derived from a number of sources, including entered by an operator and/or received from a blood pressure sensor.

$$MAP \approx BP_{dia} + \frac{(BP_{sys} - BP_{dia})}{3} \text{ (mmHg)}$$

Systemic Vascular Resistance

Systemic Vascular Resistance (SVR) can be calculated using the following equation. In this equation, MAP is Mean Arterial Pressure, CVP is Central Venous Pressure (mmHg, normally 0) and CO is Cardiac Output. It will be appreciated that these parameters may be predetermined by: being entered by an operator and/or separately calculated.

$$SVR = 80 \times \frac{(MAP - CVP)}{CO} \text{ (dyne} \cdot \text{s} \cdot \text{cm}^{-5}\text{)}$$

Systemic Vascular Resistance Index

A Systemic Vascular Resistance Index (SVRI) can be calculated using the following equation. In this equation, SVR is Systemic Vascular Resistance and BSA is Body Surface Area.

SVRI=SVR×BSA(dyne·s·cm$^{-5}$·m$^2$)

Spot Oxygen Saturation

Spot Oxygen Saturation (SpO$_2$) can be obtained directly from a pulse oximeter as a percentage, typically without further calculation.

Oxygen Delivery (DO$_2$)

Simplified Oxygen Delivery (DO$_2$) can be calculated using the following equation. It is typical that (PaO$_2$×0.023) is small $$DO_{2(mlO2/L)} = 1.34 \times \frac{Hb_{g/dL}}{100} \times \frac{Sp\ O2_\%}{100} \times 1000 \times CO_{L/min}$$

It will be appreciated that, by way of example, the theoretical maximum oxygen carrying capacity is 1.39 ml O$_2$/g Hb, but direct measurement gives a capacity of 1.34 ml O$_2$/g Hb. The 1.34 term is also known as Hüfner's constant. The oxygen content of blood is typically measured as the volume of oxygen carried in each 100 ml blood.

An estimate of oxygen content can be calculated by: (O$_2$ carried by Hb)+(O$_2$ in solution)=(1.34×Hb×SpO$_2$×0.01)+ (0.023×PaO$_2$), where:

SO$_2$ is the percentage saturation of Hb with oxygen

Hb is the haemoglobin concentration in grams pre 100 ml blood

PO$_2$ is the partial pressure of oxygen (0.0225=ml of O$_2$ dissolved per 100 ml plasma per kPa, or 0.003 ml per mmHg)

It will be appreciated that, for a normal adult male, the oxygen content of arterial blood can be calculated as follows, given arterial oxygen saturation (% SpO$_2$)=100%, Hb=15 g/100 ml and arterial partial pressure of oxygen (PaO$_2$)=13.3 kPa. In this example the oxygen content of arterial blood (CaO$_2$) is:

CaO$_2$=20.1+0.3=20.4 ml/100 ml

Similarly the oxygen content of mixed venous blood can be calculated. Given typical values of mixed venous oxygen saturation (SvO$_2$)=75% and venous partial pressure of oxygen (PvO$_2$)=6 kPa, oxygen content of mixed venous blood can be calculated as:

CvO$_2$=15.2+0.1=15.2 ml/100 ml

Oxygen delivery is the amount of oxygen delivered to the peripheral tissue, and is obtained by multiplying the arterial oxygen content (CaO$_2$) by the cardiac output (Q). For example, where CaO$_2$=20.1 ml/100 ml and Q=5 l/min: Oxygen delivery (DO$_2$) is equal to 1005 ml/min.

The amount of returned Oxygen is given by the product of the mixed venous oxygen content (CvO$_2$) and the cardiac output. For example, where $CvO_2$=15.2 ml/100 ml and Q=5.0 l/min: Oxygen return is equal to 760 ml/min Oxygen uptake is the amount of oxygen taken up by the tissues that can be calculated from the difference between oxygen delivery and the oxygen returned to the lungs in the mixed venous blood.

Thus Oxygen uptake ($VO_2$) can be expressed as (oxygen delivery)−(oxygen return). According to the example values above $VO_2$=1005−760=245 ml/min It will be appreciate that a goal of the cardio respiratory system is to deliver adequate oxygen to the tissues to meet their metabolic requirements, a balance between $VO_2$ and $DO_2$. This balance between oxygen uptake by the body tissues and oxygen delivery to them can be assessed by:

The oxygen content of mixed venous blood $CvO_2$, which is normally about 15 ml/100 ml.

The extraction ratio, which is the ratio of $VO_2$ to $DO_2$ expressed as a percentage. Normally the extraction ratio is about 25% but can double to 50% if tissue demand increases.

It will be appreciates that the above indices are dependent on mixed venous saturation (SvO2), and cardiac output.

Cardiac Power

Cardiac Power (CPO) can be expressed mathematically by the following equation.

$$CPO_{Watts} = \frac{(MAP_{mmHg} - CVP_{mmHg}) \cdot CO_{L/min}}{450.037}$$

Stroke Work

Stroke Work (SW) can be expressed mathematically by the following equation.

$$SW_{mJ} = \frac{60}{450}(MAP_{mmHg} - CVP_{mmHg}) \cdot SV_{ml}$$

Flow Time Corrected (FTc)

Flow Time Corrected (FTc) can be expressed mathematically by the following equation (based on Bazett's formula).

$$FT_{c_{ms}} = \frac{FT_{ms}}{\sqrt{RR_s}}$$
$$= \frac{FT_{ms}}{\sqrt{60/HR_{bpm}}}.$$

Noninvasive Pressure Volume Loops

In another embodiment, real time noninvasive measurement of flow and central pressure can be combined to generate noninvasively acquired pressure volume loops. Such pressure volume loops are particularly important for understanding the cardiovascular function and have previously been derived from catheter based measurements. Changes in the loop over time and the gradients of various sections of the loop are important both for diagnosis and for evaluation of therapy. A noninvasive pressure volume loop that can be generated beat to beat can be an important and novel tool for improved understanding of cardiovascular physiology and therapy.

Correction Factors and Conversions

In an embodiment, Flow Tracer derived Cardiac Output values can be corrected to substantially match the Touch Point derived Cardiac Output values. Flow Tracer Cardiac Output (CO) can be increased without changing the Touch Point derived CO. This is achieved with a combination of correction factors that slightly modify the OTD and vti. Touch Point derived CO value is unchanged by the correction factors. In an embodiment, the OTD is increased by 2.4695%. This increases the cross sectional area of the valve by about 5%. The vti for Flow Tracer is increased by 5%. The vti for Touch Point is reduced by 5% to compensate for the increase in OTD and cross sectional area. These result in the CO value for Flow Tracer is an increasing by 10%.

Correction factors, by way of example only, can be defined as follows:

FlowTracer vti correction factor $KFT_{vti}$ 1.05
OTD correction factor $K_{OTD}$ $\sqrt{1.05}$=1.0246950766
TouchPoint vti correction factor $KTP_{vti}$ 1/1.05=0.95238095238

The following equation can be used to convert between centimeters to/from feet and inches.
1 inch=2.54 cm
1 foot=12 inches The following equation can be used to convert between kilograms to/from pounds and ounces.
1 pound=0.45359237 kg
1 pound=16 ounces Measurement Range A typical range of each measurement can be used to determine default ranges, particularly for graphing purposes. The default graphing scale can include the normal range, with a margin to include most values obtained in clinical practise.

According to an embodiment, by way of example only, a table below provides a range for selected measurements.

| Measurement | Minimum | Maximum | Default Minimum Scale | Default Maximum Scale |
|---|---|---|---|---|
| Vpk (AV) | 1 | 1.4 | 0.2 | 2 |
| Vpk (PV) | 0.6 | 0.9 | 0.2 | 2 |
| Pmn | | | 0.8 | 3 |
| Vti | 21 | 31 | 5 | 40 |
| HR | 70 | 100 | 30 | 160 |
| MD | 15 | 22 | 5 | 30 |
| ET | 35 | 47 | 20 | 60 |
| SV | 65 | 100 | 20 | 150 |
| CO | 5 | 7 | 2 | 15 |
| CI | 2.4 | 3.6 | 1 | 7 |
| SVR | 1000 | 1600 | 500 | 2000 |
| SVRI | 2000 | 3100 | 1000 | 4000 |
| FT | 310 | 370 | 100 | 600 |
| SVI | 35 | 50 | 20 | 70 |
| SVV | 0 | 13 | 0 | 50 |
| FTc | 300 | 450 | 100 | 600 |
| SW | 404 | 1371 | 0 | 2000 |
| CPO | 0.79 | 1.32 | 0 | 3 |
| VS | 63 | 97 | 20 | 150 |
| $SpO_2$ | 95 | 99 | 90 | 100 |
| $DO_2$ | 887 | 1428 | 500 | 2000 |
| SP | 90 | 135 | | |
| DP | 50 | 90 | | |
| MAP | 69 | 99 | | |
| CVP | 3.75 | 7.5 | | |
| Hb | 12.1 (f) | 17.2 (m) | | |

This table shows typical minimum and maximum values for selected measurements, along with default minimum and maximum range values used in graphing measurements.

Typical minimum and maximum values can also depend on, or be derived from, the minimum and maximum values of other measurements. It will be appreciated that, a number of assumptions are made to do derive these values. It is an intention to generate approximate values such that appropriate default range can be selected, the simplification of these assumptions is appropriate. These assumptions include: the normal ranges were assumed to be the 95% confidence interval of a normally distributed random variable; and the measurements were considered independent. The new 95% confidence interval was determined by calculating a large number of randomly selected values, then picking the 95% confidence interval empirically.

It will be appreciated that the above embodiments provide a method and apparatus for calculating measurements for blood flow monitoring.

Interpretation

Unless specifically stated otherwise, as apparent from the following discussions, it is appreciated that throughout the specification discussions utilizing terms such as "processing", "computing", "calculating", "determining" or the like, refer to the action and/or processes of a computer or computing system, or similar electronic computing device, that manipulate and/or transform data represented as physical, such as electronic, quantities into other data similarly represented as physical quantities.

In a similar manner, the term "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

The methodologies described herein are, in one embodiment, performable by one or more processors that accept computer-readable (also called machine-readable) code containing a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. Each processor may include one or more of a CPU, a graphics processing unit, and a programmable DSP unit. The processing system further may include a memory subsystem including main RAM and/or a static RAM, and/or ROM. A bus subsystem may be included for communicating between the components. The processing system further may be a distributed processing system with processors coupled by a network. If the processing system requires a display, such a display may be included, e.g., a liquid crystal display (LCD) or a cathode ray tube (CRT) display. If manual data entry is required, the processing system also includes a source device such as one or more of an alphanumeric input unit such as a keyboard, a pointing control device such as a mouse, and so forth. The term memory unit as used herein, if clear from the context and unless explicitly stated otherwise, also encompasses a storage system such as a disk drive unit. The processing system in some configurations may include a sound output device, and a network interface device. The memory subsystem thus includes a computer-readable carrier medium that carries computer-readable code (e.g., software) including a set of instructions to cause performing, when executed by one or more processors, one of more of the methods described herein. Note that when the method includes several elements, e.g., several steps, no ordering of such elements is implied, unless specifically stated. The software may reside in the hard disk, or may also reside, completely or at least partially, within the RAM and/or within the processor during execution thereof by the computer system. Thus, the memory and the processor also constitute computer-readable carrier medium carrying computer-readable code.

Furthermore, a computer-readable carrier medium may form, or be included in a computer program product.

In alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Thus, one embodiment of each of the methods described herein is in the form of a computer-readable carrier medium carrying a set of instructions, e.g., a computer program that are for execution on one or more processors, e.g., one or more processors that are part of a component playback unit. Thus, as will be appreciated by those skilled in the art, embodiments of the present invention may be embodied as a method, an apparatus such as a special purpose apparatus, an apparatus such as a data processing system, or a computer-readable carrier medium, e.g., a computer program product. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media. Non-volatile media includes, for example, optical, magnetic disks, and magneto-optical disks. Volatile media includes dynamic memory, such as main memory. Transmission media includes coaxial cables, copper wire and fiber optics, including the wires that comprise a bus subsystem. Transmission media also may also take the form of acoustic or light waves, such as those generated during radio wave and infrared data communications. For example, the term "carrier medium" shall accordingly be taken to included, but not be limited to, solid-state memories, a computer product embodied in optical and magnetic media, a medium bearing a propagated signal detectable by at least one processor of one or more processors and representing a set of instructions that when executed implement a method, a carrier wave bearing a propagated signal detectable by at least one processor of the one or more processors and representing the set of instructions a propagated signal and representing the set of instructions, and a transmission medium in a network bearing a propagated signal detectable by at least one processor of the one or more processors and representing the set of instructions.

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being limitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

Similarly, it is to be noticed that the term coupled, when used in the claims, should not be interpreted as being limitative to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still co-operate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

The claims defining the invention are as follows:
1. A method of cardiac blood flow monitoring for a patient, said method comprising the steps of:

a) receiving a first signal indicative of the real time cardiac output for said patient;
b) processing through a computer processor said first signal to provide an estimate of the cardiac blood flow velocity out of the heart as a function of time;
c) receiving a pressure measurement indicative of the blood flow resistance through the patient;
d) calculating via a computer processor an Inotropy measure indicative of the potential and kinetic energy of the cardiac output of the patient from said blood flow velocity and said blood flow resistance;
e) using the calculated Inotropy measure to determine a treatment protocol for the patient; and
f) having the patient treated according to the treatment protocol;

wherein the first signal comprises a continuous wave Doppler signal indicative of the cardiac output of said patient and wherein processing the continuous wave Doppler signal to provide an estimate of cardiac blood flow velocity comprises estimating a time sampled maximum velocity sequence and wherein said processing the continuous wave Doppler signal to provide an estimate of cardiac blood flow velocity comprises modelling flow velocity associated with at least one heart beat cycle as a series of line segments relating velocity to time.

2. A method as claimed in claim 1, wherein said Inotropy measure includes an Inotropy Index combining a potential energy measure and a kinetic energy measure of the cardiac output.

3. A method as claimed in claim 1, wherein said Inotropy measure includes a potential energy to kinetic energy ratio.

4. A method as claimed in claim 1 wherein said Inotropy measure includes an Inotropy power measurement indicative of the time over which the cardiac output of the patient is provided.

5. A method as claimed in claim 1, wherein said estimate of blood flow velocity includes one or more measurement selected from the set comprising: Ejection Time; Heart Rate; Peak Velocity, Velocity Time Integral and Mean Pressure Gradient.

* * * * *